US00PP29720P3

(12) United States Plant Patent
Hansen

(10) Patent No.: US PP29,720 P3
(45) Date of Patent: Oct. 2, 2018

(54) ***VERONICA* PLANT NAMED 'PERFECTLY PICASSO'**

(50) Latin Name: ***Veronica spicata* L.**
Varietal Denomination: Perfectly Picasso

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 10 days.

(21) Appl. No.: 15/530,510

(22) Filed: Jan. 23, 2017

(65) Prior Publication Data

US 2018/0213699 P1 Jul. 26, 2018

(51) Int. Cl.
*A01H 5/02* (2018.01)

(52) U.S. Cl.
USPC ..... Plt./251

(58) Field of Classification Search
USPC ..... Plt./251
See application file for complete search history.

*Primary Examiner* — Anne Marie Grunberg

(57) ABSTRACT

The new and distinct cultivar of ornamental spike speedwell plant, *Veronica spicata* 'Perfectly Picasso', with upright habit, stiff upright to slightly-curved, freely-branched spikes producing steadfast medium-pink flowers from buds that begin near white buds and become medium pink, over a long period beginning early summer and deadheading may encourage possible repeat in early fall.

1 Drawing Sheet

Botanical classification: *Veronica spicata* L.
Variety denomination: 'Perfectly Picasso'.

BACKGROUND OF THE INVENTION

The present invention relates to the new and distinct cultivar of spike speedwell, botanically known as *Veronica spicata* 'Perfectly Picasso', and hereinafter referred to as the cultivar 'Perfectly Picasso' or the "new plant". The new plant was hybridized in the summer of 2012 by the inventor in the hybridizing greenhouses of a wholesale perennial nursery in Zeeland, Mich., USA, with the unreleased proprietary hybrid known only as 08-64-01B as the female parent and *Veronica* 'Red Fox' (not patented) as the male parent.

The new plant has been asexually propagated by shoot tip cuttings at the same nursery in the greenhouses in Zeeland, Mich., since the summer of 2014 with subsequent asexually propagated plants found to be identical to the original selection with all the same traits as the original seedling.

No plants of *Veronica* 'Perfectly Picasso' have been sold or disclosed by this or any other name, in this country or anywhere in the world, prior to one year from the filing of this application, with the exception of that was sold or disclosed within one year of the filing of this application and which was either derived directly or indirectly from the inventor.

BRIEF SUMMARY OF THE PLANT

*Veronica spicata* 'Perfectly Picasso' is unique from all other spike speedwell known to the inventor. Several other cultivars may have some similar traits, but this is the only variety known by the inventor to have the following characteristic combinations that establish the new plant as unique:

1. Upright habit with stiff, tall, upright to slightly-curved spikes above dense mats of medium green foliage.
2. Scapes with numerous flowers of distinctly steadfast medium-pink petals.
3. Young flower buds change from near white to medium pink before opening.
4. Freely-branched peduncles with long blooming season.

The closest comparison varieties are 'Tickled Pink' U.S. Plant Pat. No. 16,182, 'Pink Bomb' U.S. Plant Pat. No. 24,756, 'Pink Explosion' U.S. Plant Pat. No. 22,592, 'Atomic Silvery Pink Ray' U.S. Plant Pat. No. 23,938, 'Sweet Lullaby' U.S. Plant Pat. No. 23,611, 'Pink Eveline' U.S. Plant Pat. No. 18,743, 'Pink Panther' U.S. Plant Pat. No. 16,311, 'Pink Potion' U.S. Plant patent application. Ser. No. 15/330,912 and *Veronica* 'Red Fox' (not patented). The flowers of 'Tickled Pink' are a lighter pink, more bubblegum pink than the medium pink of the new plant, and the habit of the new plant is taller and less spreading. Compared with 'Pink Bomb' the new plant is slightly taller and the flower color is deeper pink. Compared with 'Pink Explosion' the new plant is taller and deeper pink in flower color. The new plant is taller and deeper pink than 'Pink Explosion', 'Atomic Silvery Pink Ray', 'Sweet Lullaby' and 'Pink Eveline'. Compared with 'Pink Panther' the new plant is taller, more upright and the flower color is slight deeper pink. Compared with 'Pink Potion' the new plant is slightly taller and less rounded in habit and the flower color has slightly less violet hue and more reddish hue. Compared with the female parent the new plant is slightly more compact and the flowers are medium pink rather than lavender purple. Compared with the male parent 'Red Fox' the new plant is taller, more upright and the flowers are more medium pink rather than fuchsia pink.

BRIEF DESCRIPTION OF THE DRAWINGS

The photographs of the new plant demonstrate the overall appearance and unique traits of 'Perfectly Picasso' as a two-year-old plant grown in a full-sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
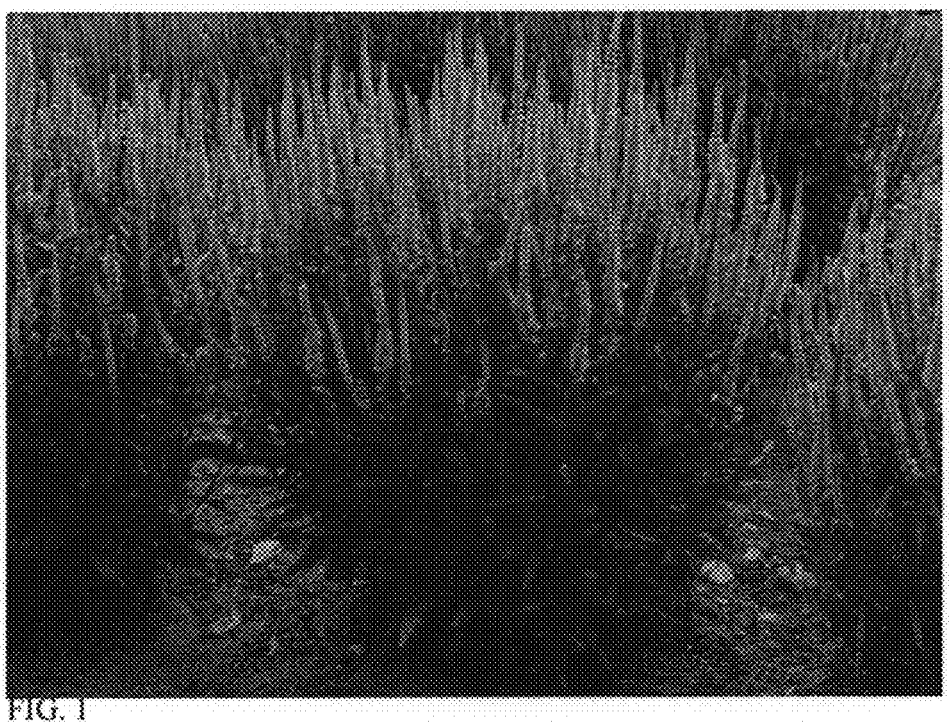
FIG. 1 shows the plant in full flower.
Figure 2:
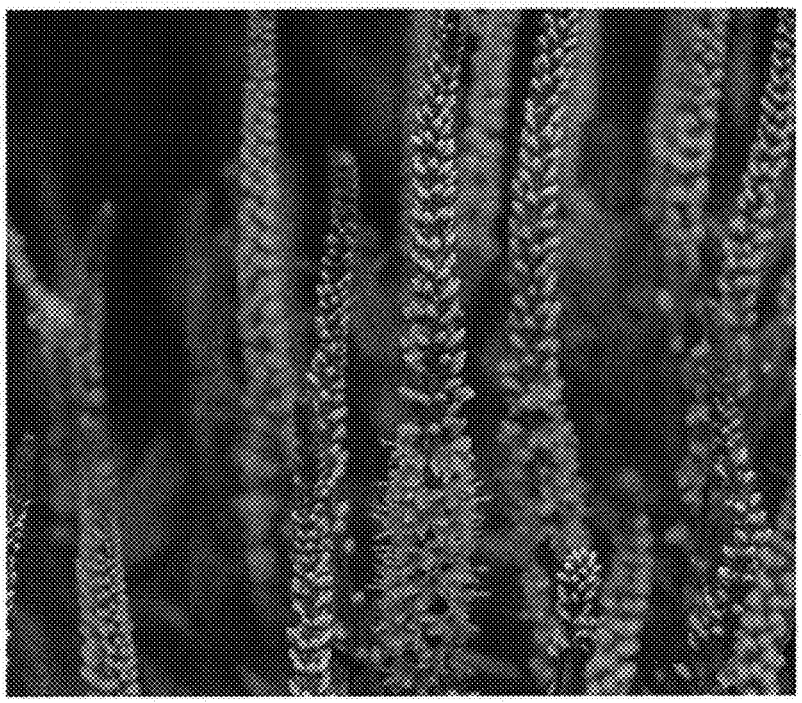
FIG. 2 shows a close-up of the flowers and buds.

The following descriptions and color references of *Veronica* 'Perfectly Picasso' are based on the 2001 edition of The Royal Horticultural Society Colour Chart except where common dictionary terms are used. *Veronica* 'Perfectly Picasso' has not been observed under all possible environments. The phenotype may vary slightly with different growing environments such as temperature, light, fertility, soil pH, moisture and maturity levels, but without any change in the genotype. The following observations and size descriptions are based on plants in a two-year-old plant grown in a full-sun trial garden of a nursery in Zeeland, Mich. with supplemental fertilizer and water as needed.

Botanical classification: *Veronica spicata;*

Parentage: Proprietary breeder known as 08-64-01B as the female (seed parent); 'Red Fox' as the male (pollen parent);

Plant habit: Hardy herbaceous perennial, compact, with average 45 stems, main stems to about 65 cm tall and clumping to about 48 cm wide; flowering beginning late June in Michigan and continuing for about 6 weeks with occasional repeat if deadheaded; Leaves: simple, flat, elliptic to lanceolate, opposite, serrated with about four to five teeth per centimeter; puberulent abaxial and glabrate to glabrous adaxial; acute apex; distal leaves with attenuate base and proximal leaves with rounded base; about 9.0 cm long by 3.1 cm wide, average about 6.0 cm long and 1.6 cm wide, decreasing in both length and width distally;

Leaf color: Mature adaxial nearest RHS 137A and abaxial nearest RHS 137C; young expanding leaves nearest RHS 144A above and below;

Veins: Reticulate, abaxial midrib costate; puberulent abaxial and glabrate to glabrous adaxial;

Vein color: Adaxial midrib nearest RHS 145A and lateral veins nearest RHS 137A; abaxial midrib nearest RHS 145A and lateral veins nearest RHS 138B;

Petiole: Simple, puberulent abaxial and adaxial; to about 3.1 cm long and 5.0 mm wide decreasing distally to an average about 3.0 mm long and 4.0 mm wide;

Petiole color: Adaxial nearest RHS 145A in center and RHS 137A on margins; abaxial nearest RHS 145A in center and nearest RHS 137C on margins;

Stem: Terete; minutely pubescent to canescent; length about 25 cm before flowers, diameter about 3.5 mm at base;

Stem color: Nearest RHS 146C;

Flower bud two days prior to opening: Convolute, narrowly oblong, obtuse apex; about 5.0 mm long and 2.5 mm diameter;

Flower bud color: One to two days prior to opening blend between RHS 73A and RHS 73B; one week prior to opening near white, lighter than RHS N155B and much lighter than RHS 62D;

Flowers: Zygomorpbic, campanulate; on heavily branched upright spikes in compressed conglomerate; numerous, approximately 600 per main spike; about 7.0 mm in diameter and about 9.0 mm deep, corolla tube about 2.0 mm long and about 2.0 mm diameter, no detectible fragrance; flowers persist individually for 4 to 6 days whether on the plant or cut petals self-cleaning, sepals persistent;

Flower timing: Early to mid-summer and continuing for about six weeks;

Flower fragrance: None detected;

Petals: Four; one larger petal above and three slightly small below and to either side; simple, entire, fused in basal 3.0 mm; each with rounded apex; larger top petal about 6.0 mm long by 3.5 mm wide, smaller side and lower petals about 6.0 mm long and 2.5 mm wide; glabrous abaxial, glabrous adaxial except with 1.0 mm long hairs in tufted band about 1.0 to 2.0 mm from base;

Petal color: Abaxial and adaxial nearest RHS 67C with corolla tube lightening to lighter than RHS 65D; adaxial tuft of hairs whiter than RHS 155D;

Androecium:

*Filaments*.—Two; divergent; glabrous; epipetalous about 1.0 mm from base; about 6.5 mm long by 0.25 mm; color nearest RHS 73B.

*Anther*.—Dorsifixed, longitudinal; ellipsoid, with acute apex and rounded base; about 2.0 mm by 1.0 mm; color nearest RHS 71A.

*Pollen*.—Abundant, globose, less than 0.1 mm; nearest RHS 4B.

Gynoecium: One, superior; persists after petal drop;

*Style*.—Straight; attitude mostly outwardly; about 6.0 mm long by 0.25 mm; color nearest RHS N81B.

*Stigma*.—Globose; about 0.3 mm in diameter; color RHS N81A.

*Ovary*.—Globose to ellipsoid; about 1.0 mm long and 0.8 mm across; color nearest RHS 145B.

Sepals: Four; lanceolate; adaxial dull, glabrous; abaxial microscopically puberulent; acute apex, base fused forming campanulate calyx, puberulent margin; about 4.0 mm long and 1.0 mm wide;

Sepal color: Abaxial and adaxial nearest RHS 138A;

Peduncle: About 45 per plant; raceme, strong, virgate, freely branched at nodes, terete: minutely pubescent to canescent; flowering portion to about 40.0 cm long and about 2.5 cm across with stem base diameter about 2.5 mm; averaging about 32.0 cm long and 2.5 mm base; freely branching at nearly every node; about 7 to 8 nodes before flowers; average internode length about 3.5 cm;

Peduncle color: Nearest RHS 146C;

Pedicel: Rigid, about 0.5 mm long and 0.2 mm wide, finely pubescent; attitude outwardly;

Pedicel color: Nearest RHS 138A;

Bract: One, subtending each flower, linear, acute apex, mostly entire, sessile, based fused to peduncle, proximal bracts about 2.2 cm long and 4.0 mm wide and decreasing distally to about 4.0 mm long and less than 1.0 mm wide;

Bract color: Nearest RHS 138A both adaxial and abaxial;

Fruit: Ellipsoid with rounded apex and base, about 3.1 mm long and 2.5 mm across; color between RHS 165A and RHS 165B;

Propagation: The plant roots from cuttings in about 2 weeks and finishes to flowering in a 3.8 liter container in 8 to 10 weeks following a vernalization period of about 8 weeks;

Hardiness, pest and disease resistance: The plant grows best with plenty of moisture and adequate drainage, but is able to tolerate some drought when mature. Hardiness at least from USDA zone 4 through 9. Disease and pest resistance beyond what is typical of that of other spike speedwell has not been observed.

I claim:

1. A new and distinct cultivar of ornamental spike speedwell plant, *Veronica spicata* 'Perfectly Picasso', as herein described and illustrated.

* * * * *